United States Patent [19]

DiNinno et al.

[11] Patent Number: 4,962,101

[45] Date of Patent: Oct. 9, 1990

[54] 2-(HETEROCYCLYLALKYL)PHENYL CARBAPENEM ANTIBACTERIAL AGENTS

[75] Inventors: Frank P. DiNinno, Old Bridge; Thomas N. Salzmann, North Plainfield, both of N.J.

[73] Assignee: Merck & Co., Inc., Rahway, N.J.

[21] Appl. No.: 396,163

[22] Filed: Aug. 21, 1989

[51] Int. Cl.$^5$ .................... C07D 487/04; A61K 31/40
[52] U.S. Cl. ..................................... 514/210; 540/302
[58] Field of Search .......................... 540/302; 514/210

[56] References Cited

U.S. PATENT DOCUMENTS 4,260,627  4/1981  Shih ...................................... 540/210
4,543,257  9/1985  Cama ..................................... 540/210

FOREIGN PATENT DOCUMENTS 0277743  8/1988  European Pat. Off. ............ 540/210

Primary Examiner—Robert Gerstl
Attorney, Agent, or Firm—Raymond M. Speer; Hesna J. Pfeiffer

[57] ABSTRACT

Carbapenems having the formula:

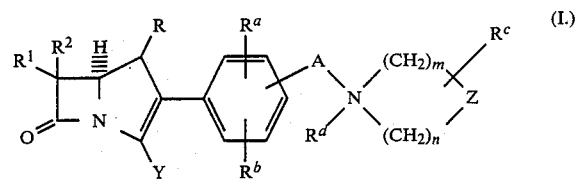

are useful antibacterial agents.

12 Claims, No Drawings

2-(HETEROCYCLYLALKYL)PHENYL CARBAPENEM ANTIBACTERIAL AGENTS

BACKGROUND OF THE INVENTION

The present invention relates to antibacterial agents of the carbapenem class, in which the 2-position side-chain is characterized by a phenyl moiety, optionally substituted, to which is attached, usually through an alkyl bridge, a nitrogen containing heterocyclic group, with attachment being through the nitrogen atom, as described in more detail further below.

Thienamycin was an early carbapenem antibacterial agent having a broad spectrum; it has the following formula:

Later, N-formimidoyl thienamycin was discovered; it has the formula:

The 2-(heterocyclylheteroaryliumalkyl)phenyl carbapenems of the present invention have an antibacterial potency equal to or greater than, in most cases, that of either thienamycin or N-formimidoyl thienamycin. The compounds of the present invention are also more resistant than thienamycin or N-formimidoyl thienamycin to degradation by the dehydropeptidase enzyme DHP-I, thus permitting greater therapeutic application of the compounds.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

However, these compounds belong to a different class from those of the present invention and are distinguished by different physiological properties.

SUMMARY OF THE INVENTION

The present invention provides novel carbapenem compounds of the formula:

wherein:
R is H or $CH_3$;
$R^1$ and $R^2$ are independently H, $CH_3$—, $CH_3CH_2$, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^a$, $R^b$, and $R^c$ are independently selected from the group consisting of
(a) a trifluoromethyl group: $-CF_3$;
(b) a halogen atom: —Br, Cl, —F, or —I;
(c) $C_1$-$C_4$ alkoxy radical: $-OC_{1-4}$ alkyl;
(d) a hydroxy group: —OH,
(e) ($C_1$-$C_6$ alkyl) carbonyloxy radical:

$$\overset{O}{\underset{\|}{OCC_{1-6} \text{ alkyl}}};$$

(f) a carbamoyloxy radical which is unsubstituted or substituted on nitrogen with one or two alkyl groups:

$C_1$-$C_4$ alkyl groups: $-OCN\overset{R^y}{\underset{R^z}{\diagdown}}$ with $\overset{O}{\|}$ where $R^y$ and $R^z$ are independently H or $C_{1-4}$ alkyl;
(g) a $C_1$-$C_6$ alkylthio radical, $C_1$-$C_6$ alkylsulfinyl radical or $C_1$-$C_6$ alkylsulfonyl radical:

$$-SC_{1-6}^{(O)_n}$$

alkyl where n=0–2, and the alkyl portion is optionally substituted by cyano;

(h) a sulfamoyl group which is unsubstituted or substituted on nitrogen by one or two $C_1$-$C_4$ alkyl groups:

$-SO_2N\overset{R^y}{\underset{R^z}{\diagdown}}$ where $R^y$ and $R^z$ are as defined above;
(i) an amino group, or a mono ($C_1$-$C_4$ alkyl) amino or di($C_1$-$C_4$ alkyl)amino group:

where $R^y$ and $R^z$ are as defined above;
(j) a formylamino group:

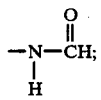

(k) $(C_1-C_6$ alkyl)carbonylamino radical:

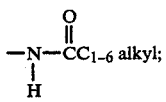

(l) a $(C_1-C_4$ alkoxy) carbonylamino radical:

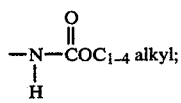

(m) a ureido group in which the terminal nitrogen is unsubstituted or substituted with one or two $C_1-C_4$ alkyl groups:

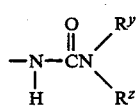

where $R^y$ and $R^z$ are as defined above;
(n) a sulfonamido group:

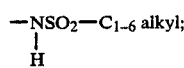

(o) a cyano group: —CN;
(p) a formyl or acetalized formyl radical:

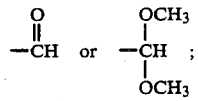

(q) $(C_1-C_6$ alkyl)carbonyl radical wherein the carbonyl is free or acetalized:

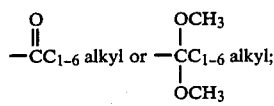

(r) phenylcarbonyl;
(s) a hydroximinomethyl radical in which the oxygen or carbon atom is optionally substituted by a $C_1-C_4$ alkyl group:

where $R^y$ and $R^z$ are as defined above;
(t) a $(C_1-C_6$ alkoxy)carbonyl radical;

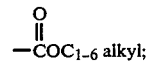

(t) a carbamoyl radical which is unsubstituted or substituted on nitrogen by one or two $C_1-C_4$ alkyl groups:

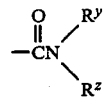

where $R^y$ and $R^z$ are as defined above:
(v) an N hydroxycarbamoyl or N($C_1-C_4$ alkoxy)carbamoyl radical in which the nitrogen atom may be additionally substituted by a $C_1-C_4$ alkyl group:

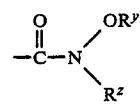

where $R^y$ and $R^z$ are as defined above;
(w) a thiocarbamoyl group:

(x) an amidino group

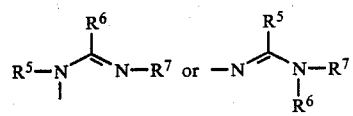

where $R^5$, $R^6$ and $R^7$ are independently hydrogen, $C_1-C_4$alkyl or wherein two of the alkyl groups together form a $C_2-C_6$alkylidene radical optionally interrupted by a heteroatom and joined together to form a ring;
(y) a carboxamidino group

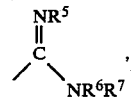

where $R^5$, $R^6$ and $R^7$ are as defined above;
(z) a guanidinyl group where $R^6$ in (a) above is $NR^8R^9$ and $R^8$ and $R^9$ are as defined for $R^5$ through $R^7$ above;
(aa) hydrogen;
(ab) $C_2-C_6$ alkenyl radical;
(ac) an unsubstituted or substituted $C_2-C_6$ alkynyl radical;
(ad) $C_3-C_7$ cycloalkyl radical;
(ae) $C_3-C_7$ cycloalkyl methyl radical;
(af) $C_5C_7$ cycloalkenyl radical;

(ag) phenyl, except that only $R^c$ may be phenyl;
(ah) $C_1-C_6$ alkyl radical;
(ai) $C_1-C_4$ alkyl monosubstituted by one of the substituents (a)-(ag) above;
(aj) an anionic function selected from the group consisting of:
phosphono [P=O(OM$^c$)$_2$]; alkylphosphono {P=O(OM$^c$) [O(C$_1$-C$_4$ alkyl)]}; alkylphosphinyl [P=O(OM$^c$)-(C$_1$-C$_4$alkyl)]; phosphoramido [P=O(OM$^c$)N(R$^y$)R$^z$ and P=O(OM$^c$)NHR$^x$]; sulfino (SO$_2$M$^c$); sulfo (SO$_3$M$^c$); acylsulfonamides selected from the structures CONM$^c$SO$_2$R$^x$, CONM$^c$SO$_2$N(R$^y$)R$^z$, SO$_2$NM$^c$CON(R$^y$)R$^z$; and SO$_2$NM$^c$CN, where $R^x$ is phenyl or heteroaryl, where heteroaryl is as defined below except that there is no quaternary nitrogen and attachment through nitrogen is optional, and the phenyl and heteroaryl are optionally mono substituted by $R^q$; $M^c$ is hydrogen or an alkali metal; $R^y$ and $R^z$ are as defined above; where $R^q$ is a member selected from the group consisting of —OH; —OCH$_3$—: —CN; —C(O)NH$_2$; —OC(O)NH$_2$; —OC(O)N(CH$_3$)$_2$; —SO$_2$NH$_2$; —SO$_2$N(CH$_3$)$_2$; —SOCH$_3$; —F, —CF$_3$; tetrazolyl; and —COOM$^a$, where $M^a$ is hydrogen, alkali metal, methyl or phenyl;

$R^d$ is $C_1-C_4$ alkyl, making the nitrogen atom of the N-heterocyclyl moiety to which it is attached quaternary: or it may be absent;

A is para (p) or meta (m) with respect to the point of attachment of the phenyl ring to the carbapenem nucleus, and is (CH$_2$)$_m$—Q—(CH$_2$)$_n$, where m is 0 to 2 and n is 1 or 2; and Q is a covalent bond; O; S; SO; or SO$_2$;

Z is a member selected from the group consisting of CH$_2$, O, S, SO, SO$_2$, N(R'), and $^+$N(R')(R''), where R' and R'' are independently hydrogen, C$_1$-C$_4$ alkyl, or oxo; provided that where $R^d$ is not absent, Z cannot be $^+$N(R')(R'');

m is 2 or 3; n is 1 or 2; and
Y is selected from:
(i) COOH or a pharmaceutically acceptable ester thereof;
(ii) COOM wherein M is an alkali metal or other pharmaceutically acceptable salt;
(iii) COOM wherein M is a negative charge in the case where a permanent positive charge exists elsewhere in the molecule.

The overall molecule must be electronically balanced. Since a quaternary nitrogen may be present in the compounds of the present invention, a balancing anion must also be present. This is usually accomplished by having Y be COO$^-$. However, where Y is, e.g; a pharmaceutically acceptable ester, a counterion (anion) Z$^-$ must be provided, or alternatively, an anionic substituent might be utilized. Further, it is within the scope of this invention to utilize an anionic substituent where the quaternary nitrogen is already balanced by Y= COO$^{31}$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

Under the definition of "Y", the term "pharmaceutically acceptable ester or salt" refers to those salt and ester forms of the compounds of the present invention which would be apparent to the pharmaceutical chemist, i.e., those which are non toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug. Since the compounds of the present invention may be carboxylates, the salts would be cations such as benzathine, chloroprocaine, choline, diethanolamine, meglumine and procaine. The metallic cations such as aluminum, calcium, lithium, magnesium and zinc are potential choices. The alkali metal cations sodium and potassium are specifically defined. It will also be noted that the compounds of the present invention are potentially internal salts or zwitterions, since under physiological conditions the carboxyl group may be anionic, and this electronic charge will be balanced off internally against the cationic charge of the heteroarylium group. Where this is not the case, it is recognized that a counterion must be present. This counterion is selected from the group of suitable pharmaceutical anions, e.g., chloride, phosphate and tartrate.

It is preferred that when one of $R^1$ or $R^2$ is H, the other is (R)—CH$_3$CH(OH)— or (R)—CH$_3$CH(F)—, and (R)—CH$_3$CH(OH)— is most preferred. Further it is preferred that the configuration at C-6 is (S), and that at C-5 is (R).

Representative A groups are —CH$_2$—, —CH$_2$CH$_2$—, and —OCH$_2$CH$_2$—. Preferred is —CH$_2$—.

Representative $R^c$ groups are —CH$_3$, —CH$_2$CH$_3$, —(CH$_2$)$_3$CH$_3$, —OCH$_3$, —SCH$_3$, —COOH, —NHCH$_2$COOH, —OH, —CH$_2$OH, —CH$_2$COOH, —CH$_2$CH$_2$COOH, —CH$_2$CONH$_2$, —CH$_2$CH$_2$S$^+$(CH$_3$)$_2$, —CH$_2$CH$_2$SO$_3$H, —CONH$_2$, —SO$_2$NH$_2$, —SO$_3$H, —NH$_2$, —N(CH$_3$)$_2$, —CON(CH$_3$)$_2$, —NHCH$_3$, —CH$_2$NH$_2$, —CN, —CH$_2$CN, —CH$_2$SCH$_3$, —CH$_2$SO$_3$, —CH$_2$SOCH$_3$, —CH$_2$SO$_2$CH$_3$, —SO$_2$CH$_3$, —SOCH$_3$, —CH$_2$OCH$_3$,

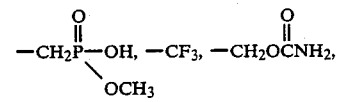

—CH$_2$SO$_2$NH$_2$, —SCH$_2$CH$_2$CN, Br, C$_1$, F, —SCF$_3$, —CH$_2$SCF$_3$, and —SCH$_2$CF$_3$.

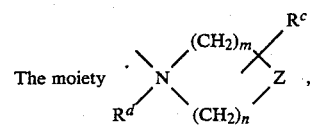

a central feature of the compounds of the present invention, defines a nitrogen containing heterocyclic structure joined to the 2-phenyl sidechain of the overall nucleus by a bridging element "A", which is directly attached to the nitrogen atom. This nitrogen atom may be quaternary, in which case $R^d$ is other than absent. The heterocyclic moiety is non aromatic, i.e., there is no unsaturation anywhere in the heterocyclic ring. The ring size may vary from 5-membered to 7-membered, depending upon the definitions of "m" and "n". A second heteroatom may be present, and is defined by the entity "Z". Thus, the second heteroatom may be O, S, or N, including oxygenated species of S, as well as substituted species of N, defined by R' and R''. This second nitrogen atom may be quaternary, but it is not desired to have both nitrogen atoms quaternary at the same time. Accordingly, the specification recites that where $R^d$ is not absent, i.e., where the first nitrogen atom (attached to "A") is quaternary, then the second nitrogen atom cannot be quaternary, i.e., Z cannot be $+N(R')(R'')$.

With regard to all of the preferred substituents described above, the following compounds are preferred embodiments of the present invention:

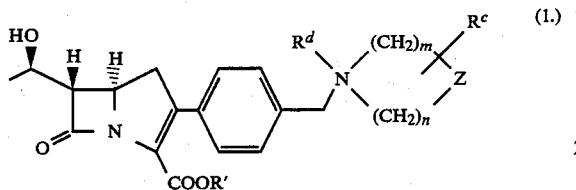
(1.)

where the nitrogen containing heterocyclic moiety is selected from:

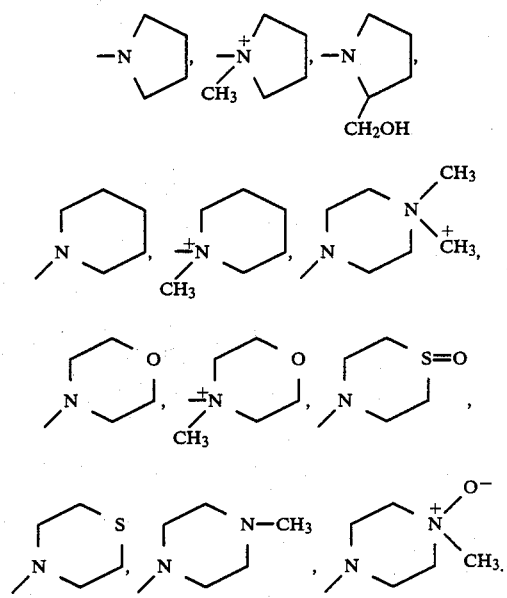

where R' is a negative charge −, or a pharmaceutically acceptable salt or ester.

While R═H is usually preferred, there are instances in which R═CH$_3$ may provide improved chemical stability, water solubility, or Pharmacokinetic behavior. The substituent R═CH$_3$ may be of either configuration, i.e., the α or β-stereoisomer.

For most of the compounds exemplified herein, the R substituent is hydrogen. This is the result not only of a more facile synthesis for such compounds, but also of a preference for R═hydrogen based on the superior antibacterial activity of such compounds.

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above include non toxic acid addition salts. In those cases where the Formula I compounds possess a basic functional group, they can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene sulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil soluble or dispersible products are thereby obtained.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The compounds of the present invention are valuable antibacterial agents active against various Gram positive and Gram negative bacteria and accordingly find utility in human and veterinary medicine. Representative pathogens which are sensitive to the antibacterial agents of the present invention include various species or strains of the following: *Staphylococcus, Enterococcus, Escherichia coli, Klebsiella, Enterobacter, Bacillus, Salmonella, Pseudomonas, Serratia, Proteus,* and *Bacterium.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections, and particularly urinary tract infections, a dose of 250 mg t.i.d. or q.i.d. is recommended.

For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require use of a DHP inhibitor. However, such use is optional and contemplated to be a part of the present invention. Inhibitors of DHP and their use with carbapenem antibacterial agents are disclosed in the prior art [see European Patent Applications No. 79102616.4 filed July 24, 1979 (Patent No. 0 010 573); 79102615.6, filed July 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use are further embodiments of the present invention.

DETAILED DESCRIPTION OF THE INVENTION

The 2-(heterocyclylalkyl)phenyl carbapenem compounds of the present invention may be prepared in accordance with well known procedures in the art. Particularly useful are the following synthetic schemes in which the symbols R, $R^1$, $R^2$, $R^a$, $R^b$, and A are as defined above, and

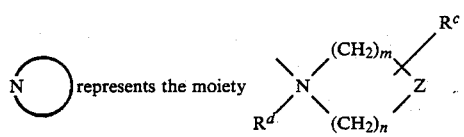

A. Heterocyclylalkylphenyl addition:

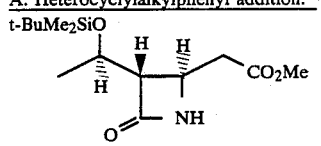

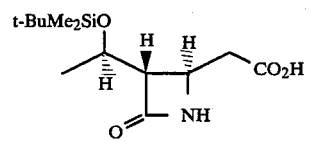
↓ b
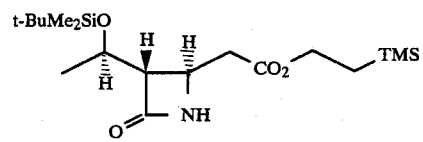
↓ c
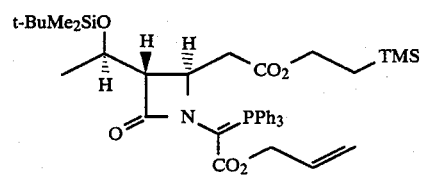
↓ d
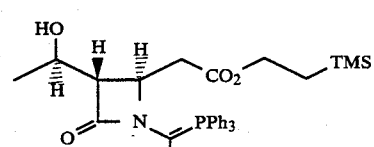
↓ e
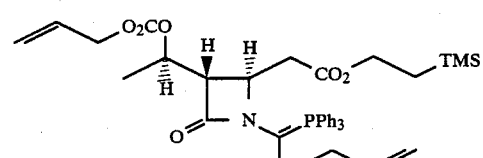
↓ f
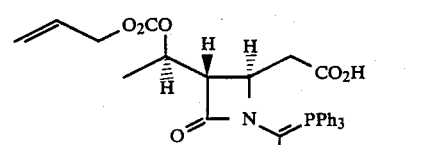
↓ g

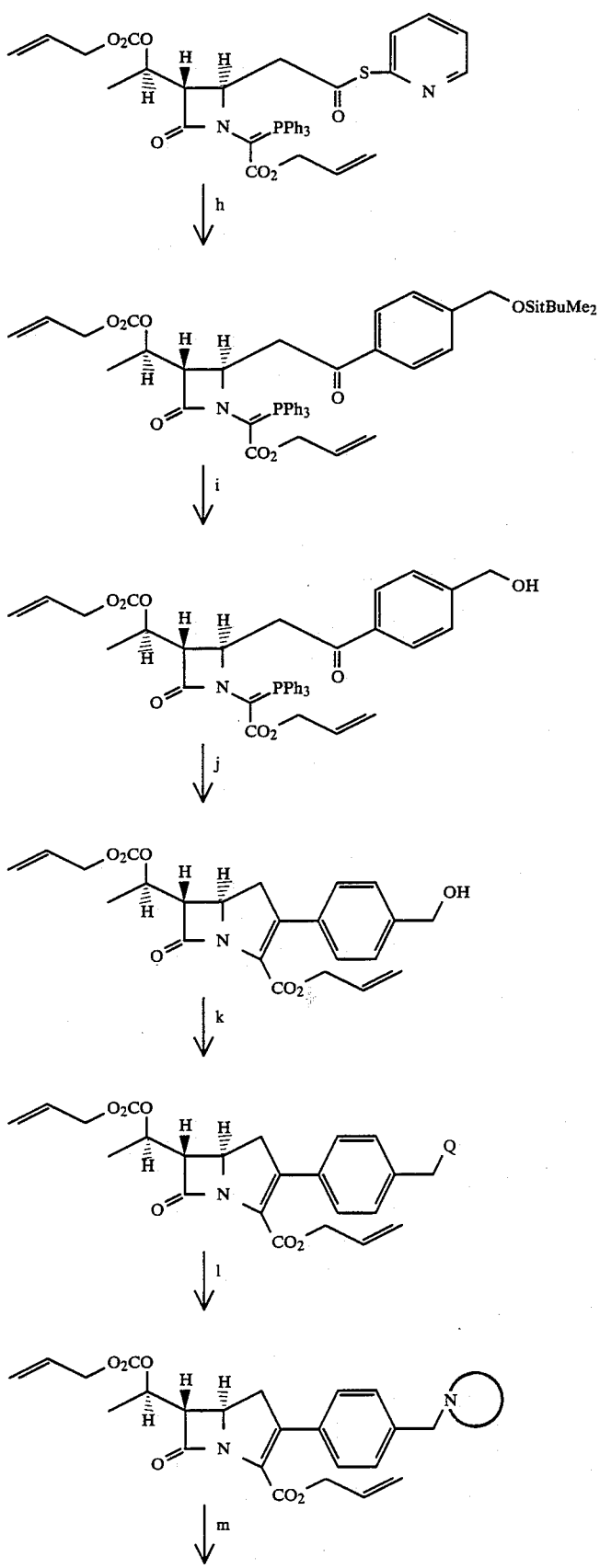

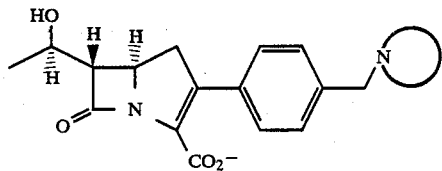

B. Quaternization:

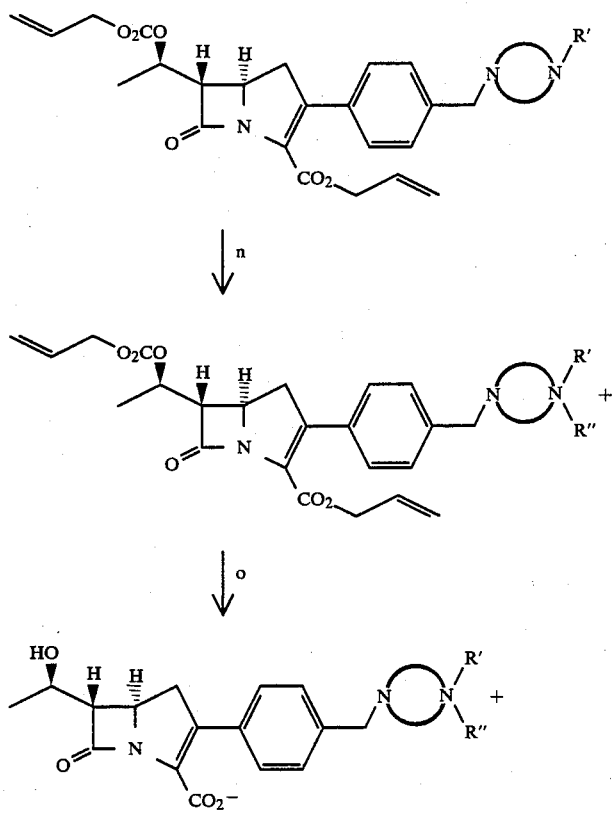

where R' and R" are defined above
a. NaOH/MeOH
b. carbonyl diimidazole
c. OHCCO$_2$;
   SOCl$_2$;
   Ph$_3$P
d. 6N HCl/MeOH
e. ClCO$_2$<img>.DMAP
f. nBu$_4$NF
g. Pyr-SS-Pyr, Ph$_3$P
h. p-BrMg—Ph—CH$_2$OSi(Me)$_2$t-Bu
i. H$_2$SO$_4$/MeOH
j. xylenes, 145° C.
k. activate (Q = —OMs, —OTf, —I)

l. N m. (Ph$_3$P)$_4$Pd, Ph$_3$P
   C$_7$H$_{15}$CO$_2$H
   C$_7$H$_{15}$CO$_2$K
n. MeI or MCPBA
o. Pd(O)

The steps for preparing the 2-phenyl carbapenem intermediate are well known in the art and are explained in ample detail in U.S. Pat. Nos. 4,260,627 and 4,543,257, which are incorporated herein by reference. Addition of the heterocyclyl alkyl moiety is as represented in the schematic diagram above.

The bridging element "A" is already in place when the phenyl group becomes a part of the carbapenem compound at the time of cyclization. In the preferred embodiments of the present invention, the bridgeing element "A" is simply alkyl. However, it is also an embodiment of the present invention to include a heteroatom in the alkyl chain, as defined further above. Preparation of such a heteroatom-containing alkyl bridge is in accordance with the following synthetic scheme:

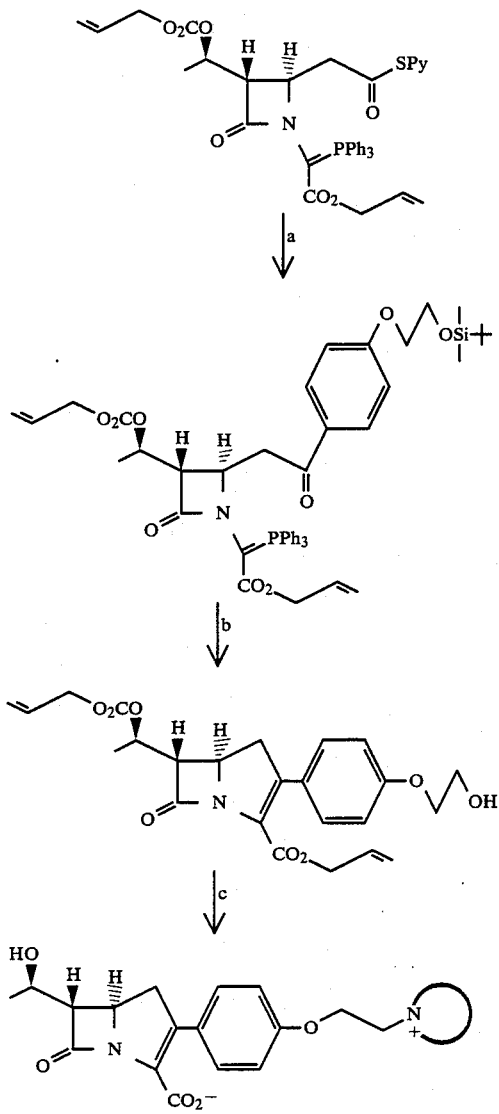

a. p-BrMg—PhOCH₂CH₂OSi(Me)₂t-Bu; THF, 0° C.
b. (1) H₂SO₄; MeOH, 0° C. (2) xylenes, 160° C.

c. (1) N◯ ; (CH₃SO₂)₂O, CH₂Cl₂, 0° C. (2) Pd(O)

The bridging element terminates in a hydroxyl group which is then changed to an active leaving group, e.g., iodide. Treatment with the desired heterocyclic reactant directly provides the heterocyclylalkylphenyl sidechain. More particularly, three alternative procedures may be utilized for addition of the heterocyclyl group.

The step of activating the phenyl-A-OH groups may be carried out in accordance with well-known procedures, some of which are exemplified in the following equations:

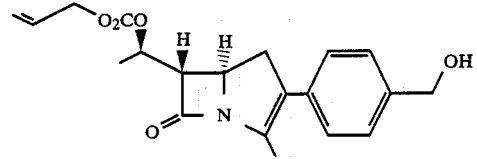

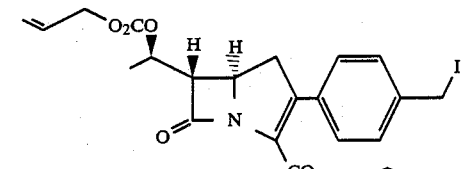

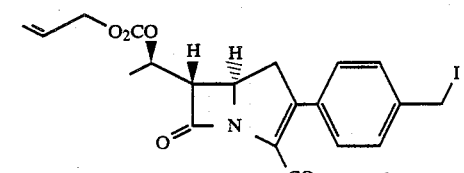

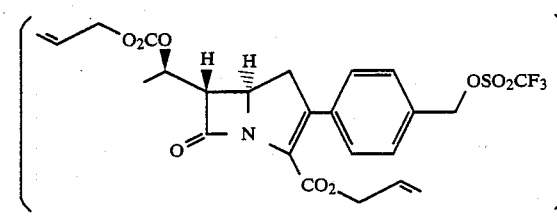

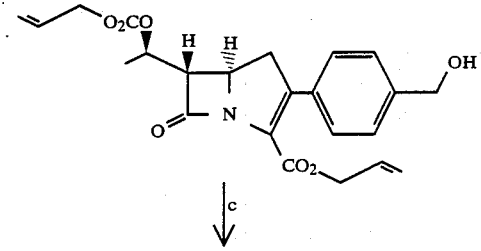

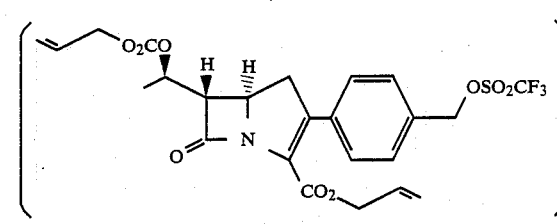

a. (1) MsCl, (2) NaI; or (PhO)₃PMe⁺I⁻
b. AgOSO₂CF₃
c. (CF₃SO₂)₂O

In words relative to the equations, the hydroxyl group may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may be converted to the more reactive iodide derivative by treatment with sodium iodide in a suitable solvent, e.g., acetone, at reduced or ambient temperatures. Alternatively, the hydroxyl group may be directly converted into the iodide group by common methods known in the art. For example, treatment of the hydroxyl group with methyl triphenoxyphosphonium iodide in a suitable solvent, such as dimethylformamide, at reduced or ambient temperatures, directly provides the desired iodide. Further, the hydroxyl group may be converted into the very reactive trifluoromethanesulfonate group. However, such an activating group cannot be isolated by conventional techniques but may be formed and used in situ. Thus, treatment of the hydroxyl group with trifluoromethanesulfonic acid anhydride in the presence of, usually, the reacting heterocyclyl base in a suitable solvent, such as dichloromethane, at reduced temperatures provides for the in situ generation of this activating group. Alternatively, the trifluoromethanesulfonate group may be generated in situ from the iodide group by treatment with excess silver trifluoromethanesulfonate in a suitable solvent, e.g., acetonitrile, at reduced temperatures.

Once the desired activation has been carried out, introduction of the heterocyclyl group can then proceed. One of the following three procedures has been found suitable for such introduction.

Method A:

The activated group is iodide and the addition of the heterocyclyl group, e.g., pyrrolidinyl, is accomplished simply by treating with the corresponding heterocycle, e.g., pyrrolidine, in a suitable solvent, e.g., acetonitrile, at about 0° C.

Method B:

The activating group is trifluoromethane sulfonate and is formed in situ by treatment of the alcohol with trifluoromethanesulfonic acid anhydride in the presence of at least two equivalents of heterocycle to provide the corresponding heterocyclyl substituent in a suitable solvent, e.g., dichloromethane, at reduced temperatures.

Method C:

The activated group is trifluoromethane sulfonate which is formed in situ by treatment of the iodide derivative with excess silver trifluoromethanesulfonate in a suitable solvent. e.g., acetonitrile, at reduced temperatures. As with Method A, the heterocycle to provide the corresponding heterocyclyl substituent is simply added and displacement of the activating group then takes place directly.

Where the heterocyclyl group has one or more substituents $R^c$ and $R^d$, the most facile method of providing such a substituent is to employ as the reactant in the preparation methods described above a heterocyclyl compound which already has the desired substituent(s). Such substituted heterocyclyl compounds are readily available starting materials or may be prepared in a straight forward manner using known literature methods.

In the preparation methods described above, the carboxyl group at the 3-position remains blocked by a carboxyl covering group until the final product is prepared. Then, deblocking may be carried out in a conventional manner, with care being taken to avoid a procedure which is so harsh as to disrupt other portions of the final product molecule.

The general synthesis description above and the particular exemplifications which follow show the 6-(1-hydroxyethyl) moiety, which is preferred in most cases. However, it has been found that with certain 2-side-chain selections, the ultimate balance of favorable clinical properties in the overall molecule may be enhanced by selection of the 6-(1-fluoroethyl) moiety instead. Preparation of this and other 6-fluoroalkyl compounds within the scope of the present invention may be carried out in a straightforward manner using techniques well know in the art of preparing carbapenem antibacterial compounds. See, e.g., J. G. deVries et al; Heterocycles, 23 (8), 1915 (1985); J6-0163- 882-A (Sanraku Ocean).

For all of the compounds exemplified herein, the R substituent is hydrogen, which is preferred. However, when R=methyl, the analogous 6-(1-hydroxyethyl) and 6-(1-fluoroethyl)carbapenems of the present invention are prepared in the manner described herein utilizing the appropriately chosen synthons which are known in the art. See, for example, L. M. Fuentes, I. Shinkai, and T. N. Salzmann, JACS, 108, 4675 (1986); and BE-900-718-A (Sandoz) respectively.

In the following examples, unless otherwise stated, degrees are in Celsius (C).

EXAMPLE 1

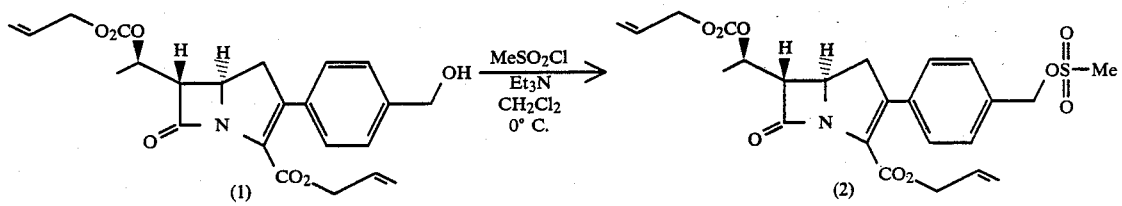

To a stirred solution of 42.7 mg (0.1 mmole) of 1 in 1 ml of sieve dried $CH_2Cl_2$ at 0° C. under a nitrogen atmosphere was added sequentially 15.2 mg (0.15 mmole) of neat $Et_3N$ and then 14.9 mg (0.13 mmole) of neat mesyl chloride. The resulting mixture was stirred for 15 minutes, and then partitioned between EtOAc, ice-$H_2O$, and some 2N HCl. The organic phase was separated, washed with saturated NaCl solution, dried over $Na_2SO_4$, filtered, evaporated, and dried in vacuo to give a quantitative yield of 2;

IR ($CH_2Cl_2$): 1780, 1745, 1725 $cm^{-1}$; 200 MHz $^1$H-NMR ($CDCl_3$) δ: 1.49 (d, J=6.4 Hz, $CH_3CH$), 2.96 (s, $CH_3SO_3$), 3.18 (dd, J=9.9, 18.1 Hz, H-1), 3.34 (dd, J=8.9, 18.1 Hz, H-1), 3.43 (dd, J=2.8, 8.1 Hz, H-6), 4.30 (dt, J=2.3, 2.8, 9.9 Hz, H-5), 4.66 (m, $CH_3CHOH$ and $CH_2CH=CH_2$), 5.26 (m, $OCH_2CH=CH_2$), 5.29 (s, $ArCH_2OSO_2$), 7.40 (s, Ar-H). UV: $\lambda_{max}^{p-diox}$ =314 nm.

EXAMPLE 2

EXAMPLE 2

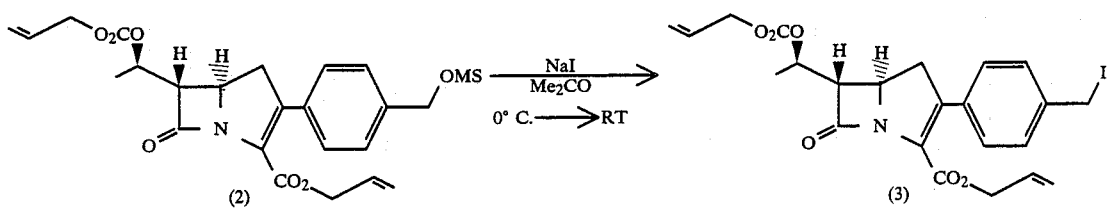

To a stirred solution of 38.8 mg (0.077 mmole) of 2 in 1 ml of acetone at 0° C. was added all at once 23 mg (0.15 mmole) of NaI. The ice-H$_2$O bath was removed and the mixture stirred further under a nitrogen atmosphere for 0.5 hour. After this time, the resulting mixture was partitioned between EtOAc, ice-H$_2$O, 5% Na$_2$S$_2$O$_4$ (aq.) solution and saturated NaCl solution. The organic phase was separated, dried over Na$_2$SO$_4$, filtered, evaporated and dried in vacuo to give 3; IR (CH$_2$Cl$_2$): 1780, 1745, 1725 cm$^{-1}$; 200 MHz $^1$H-NMR (CDCl$_3$) δ: 1.49 (d, J=7.4 Hz, CH$_3$), 3.17 (dd, J=9.8, 18.1 Hz, H-1), 3.29 (dd, J=8.7, 18.1 Hz, H-1), 3.41 (dd, J=2.9, 8.7 Hz, H-6), 4.27 (dt, J=2.9, 8.7, 9.8 Hz, H-5), 4.65 m, CH$_3$CHOH and OCH$_2$CH=CH$_2$), 5.26 (m, OCH$_2$CH=CH$_2$), 5.89 (m, OCH$_2$CH=CH$_2$), 7.32 (m, Ar-H). UV: λ$_{max}^{p-diox}$=322 nm.

EXAMPLE 3

(5R, 6S)-6-(1-(R)-hydroxyethyl)-2-(4-pyrrolidinylmethyl-phenyl)carbapenem-3-carboxylic acid

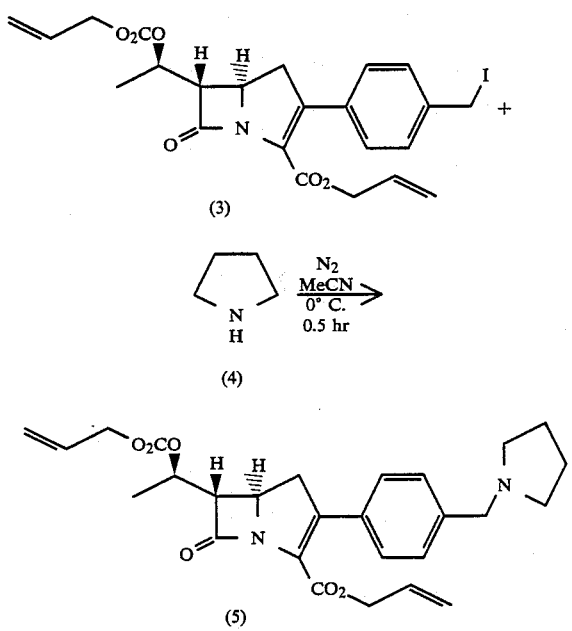

To a stirred solution of 2-(iodomethyl4-phenyl) carbapenem (3)(107.5 mg, 2×10$^{-4}$ moles) in 2 ml of sieve dried acetonitrile (CH$_3$CN) at 0 degrees C. under a nitrogen atmosphere there was added dropwise neat, distilled pyrrolidine (4) (33.4 microliters, 4×10$^{-4}$ moles). The reaction mixture was stirred at 0 degrees C. for 0.5 hr under nitrogen until the reaction was complete. The reaction mixture was then partitioned between ethyl acetate (EtOAc)/ice water (H$_2$O)/saturated sodium bicarbonate (NaHCO$_3$); and the organic phase separated, washed with saturated sodium chloride (NaCl) solution, dried over sodium sulfate (Na$_2$SO$_4$), filtered and evaporated. The final product was purified by HPLC on a 1000 micron silica gel plate eluting with ethyl acetate (EtOAc)—tetrahydrofuran (THF) in a 3:2 ratio to give 72.4 mg of oily product (5), a yield of 75.3%.

EXAMPLE 4

(5R, 6S)-6-(1-(R)-hydroxyethyl)-2-(4'-N-methyl-N-pyrrolidiniummethylphenyl-carbapenem-3-carboxylate

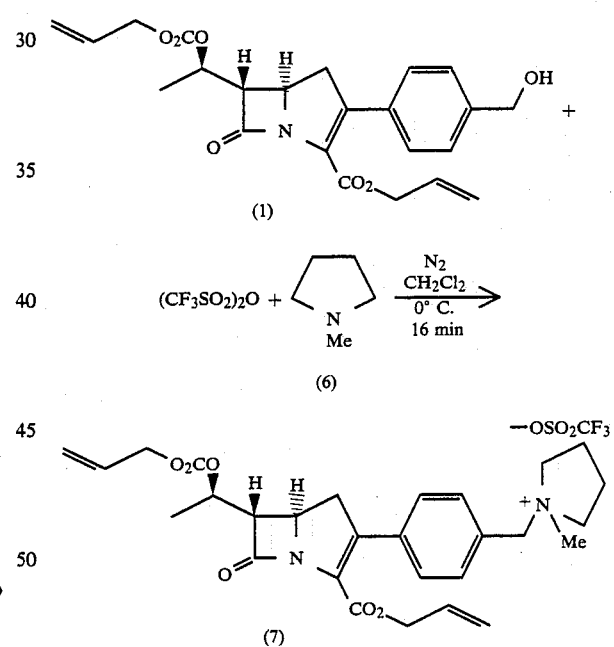

To a stirred solution of carbinol derivative (1) (74 mg, 1.73×10$^{-4}$ moles) in 2 ml of sieve dried dichloromethane (CH$_2$Cl$_2$) at 0 degrees C. under a nitrogen atmosphere was added sequentially neat N-methyl pyrrolidine (6) (32.4 mg, 3.8×10$^{-4}$ moles); and then trifluoromethanesulfonic acid anhydride [(CF$_3$SO$_2$)$_2$O] (53.7 mg, 1.9×10$^{-4}$ moles). The reaction mixture was stirred at 0 degrees C. under nitrogen for 16 min and then evaporated and dried in vacuo to give 163.5 mg or residual oil. The reaction product was partitioned between dichloromethane and water, and the organic phase was separated, washed with water and dried over sodium sulfate, filtered and evaporated to give 104 mg of foamy final product (7), a 93.1% yield.

EXAMPLE 5

(5R, 6S)-6-(1-(R)hydroxyethyl-2-(4-N-4'-thiamorpholinyl-methylphenyl)carbapenem-3-carboxylic acid

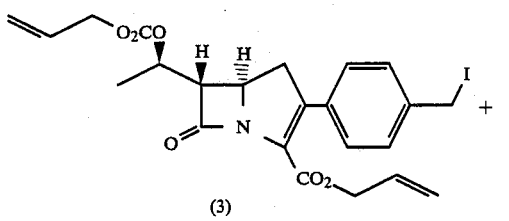

(3)

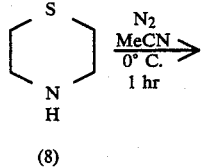

(8)

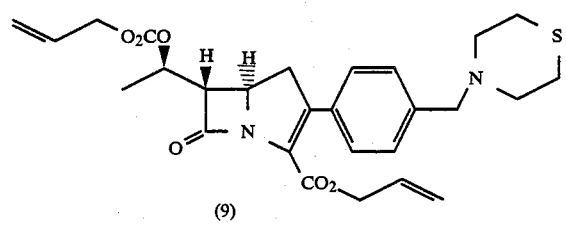

(9)

To a stirred solution of crude iodide (3) (236.3 mg, $4.4 \times 10^{-4}$ moles) in 4 ml of sieve dried acetonitrile (CH$_3$CN) at 0 degrees C. under a nitrogen atmosphere was added neat thiomorpholine (8) (90.8 mg, $8.8 \times 10^{-4}$ moles). The reaction mixture was stirred at room temperature under nitrogen for 1 hr, and then partitioned between ethyl acetate (EtOAc)/ice water. The organic phase was separated, washed with saturated sodium chloride (NaCl) solution, dried over sodium sulfate (Na$_2$SO$_4$), filtered and evaporated. The product was purified using PLC, 2 × 2000 micron plates, eluting with dichloromethane (CH$_2$Cl$_2$)—ethyl acetate (4:1), to give 222.7 mg of final product (9); a 98.8% yield.

EXAMPLE 6

(5R, 6S)-6-(1-(R)-hydroxyethyl)-2-(4-N-2-(S)-hydroxymethylpyrrolidinylmethylphenyl)carbapenem-3-carboxylic acid

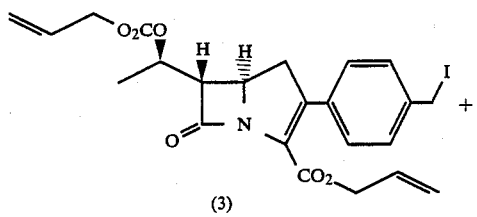

(3)

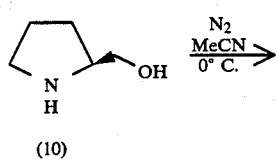

(10)

-continued

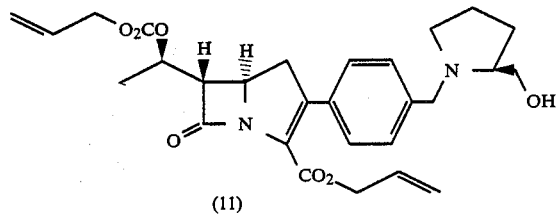

(11)

To a stirred aliquot of the stock solution of crude iodide (3) (100 mg, $1.86 \times 10^{-4}$ moles) in 1 ml of acetonitrile (CH$_3$CN) at 0 degrees C. under a nitrogen atmosphere was added neat (S)—(+)—prolinol (10) (37.7 mg, $3.7 \times 10^{-4}$ moles). The reaction mixture was stirred at 0 degrees C. under nitrogen for 50 min; 20 microliters of prolinol being added after 30 min in order to drive the reaction to completion. The product was partitioned between ethyl acetate and water and the organic phase was separated, washed with saturated sodium chloride solution, dried over sodium sulfate, filtered and evaporated. The product was purified by PLC, 2 × 1000 micron plates, eluting with ethyl acetate/tetrahydrofuran (3:1) to give 59.4 mg of final product (11), a 62.5% yield.

EXAMPLE 7

(5R, 6S)-6-(1-hydroxyethyl)-2-(N-4-methylpiperazinomethylphenyl)carbapenem-3-carboxylic acid

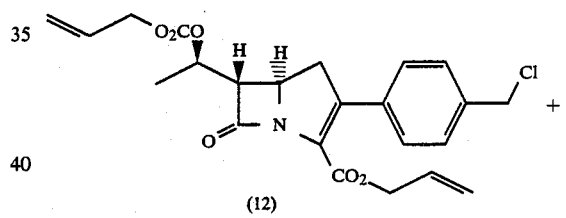

(12)

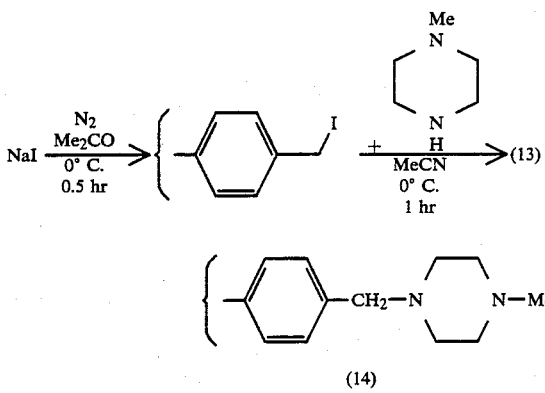

(14)

To a stirred solution of chlorobenzyl carbapenem derivative (12) (56.5 mg, $3.77 \times 10^{-4}$ moles) in 2 ml of acetone (CH$_3$COCH$_3$) at 0 degrees C. was added solid sodium iodide (NaI) (56.5 mg, $3.77 \times 10^{-4}$ moles). The reaction mixture was stirred for 0.5 hr at 0 degrees C. under nitrogen, after which the acetone was evaporated off and the residue dried in vacuo. There was then added 1.5 ml of sieve dried acetonitrile (CH$_3$CN), and the reaction mixture was stirred in an ice/water bath, after which neat N-methyl piperazine (13) (20.7 mg, 2.07×10⁻⁴ moles) was added. The reaction mixture was again stirred at 0 degrees C. under nitrogen for 3 hrs. The product was partitioned between ethyl acetate-/ice water/saturated sodium bicarbonate solution; the organic phase was separated, washed with a saturated sodium chloride solution, dried over sodium sulfate, filtered and evaporated. This product was then purified by PLC, 1×1000 micron plate, eluting with ethyl acetate/distilled tetrahydrofuran (1:1), to give 20.1 mg of the oily final product (14), a 20.2% yield.

EXAMPLE 8

(5R, 6S)-6-(1-(R)-hydroxyethyl)-2-(4-N,N-dimethyl-piperaziniummethyl)phenyl)carbapenem-3-carboxylate

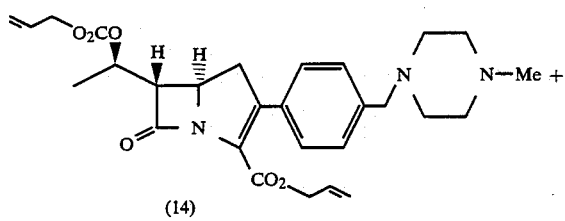

(14)

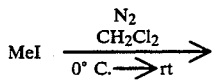

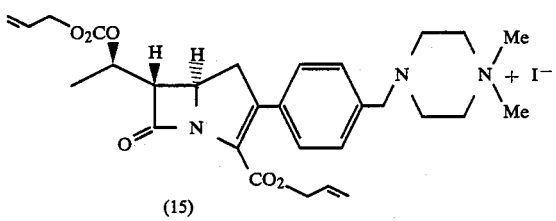

(15)

Compound (14) (23.4 mg, 4.6×10⁻⁵ moles) and methyl iodide (6.5 mg, 4.6×10⁻⁵ moles) were mixed in 0.5 ml of dichloromethane at 0 degrees C. under a nitrogen atmosphere and stirred 15 min. The ice water bath was removed; and the reaction mixture was stirred for an additional 2.5 hrs, after which it was evaporated and dried in vacuo to a foamy residue (15).

EXAMPLE 9

(5R, 6S)-6-(1-(R)-hydroxyethyl)-2-(4-N'-methyl-N'-oxide-N-piperazinomethylphenyl)carbapenem-3-carboxylic acid

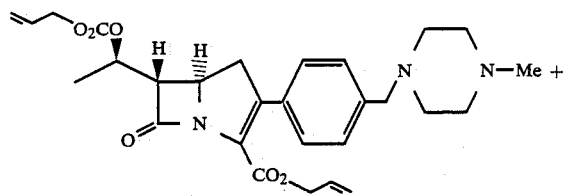

(14)

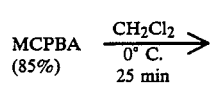

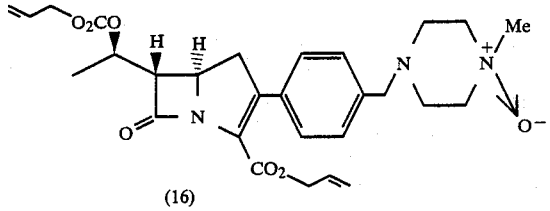

(16)

To a stirred solution of carbapenem derivative (14) (76.6 mg, 1.5×10⁻⁴ moles) in 3 ml of dichloromethane at 0 degrees C. under nitrogen was added all at once neat m-chloroperbenzoic acid (MCPBA-m-ClC₆H₅COOOH) (28.6 mg, 1.66×10⁻⁴ moles). The reaction mixture was then stirred at 0 degrees C. under nitrogen for 25 min, after which it was partitioned between dichloromethane ($CH_2Cl_2$)/ice water/saturated sodium bicarbonate ($NaHCO_3$) solution. The organic phase was separated, washed with saturated sodium chloride (NaCl) solution, dried over sodium sufate ($NaSO_4$), filtered and evaporated to give 41.4 mg of foamy product (16), a 52.4% yield.

The next two examples illustrate procedures described herein for the last step of deblocking to give the final product.

EXAMPLE 10

(5R, 6S)-6-(1-(R)-hydroxyethyl)-2-(4-N-pyrrolidinylmethyl-phenyl)carbapenem-3-carboxylic acid

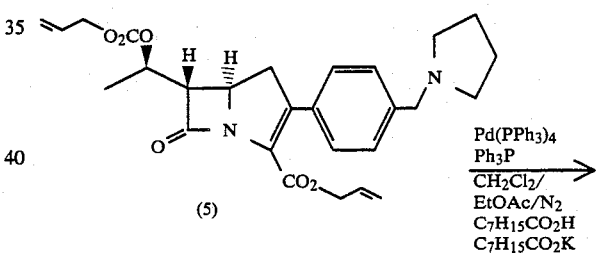

(5)

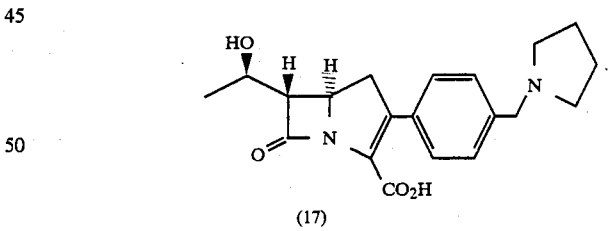

(17)

To a stirred solution of (5) (446.7 mg, 9.3×10⁻⁴ moles) in 10 ml of sieve dried dichloromethane ($CH_2Cl_2$) and 10 ml ethyl acetate (EtOAc) at room temperature was added sequentially neat 2-ethylhexanoic acid (134.2 mg, 9.3×10⁻⁴ moles), and then a solution of potassium 2-ethylhexanoate (2.05 ml, 1.02×10⁻³ moles) in ethyl acetate, followed by triphenylphosphine (73.2 mg, 2.79×10⁻⁴ moles) and tetrakis-triphenylphosphinepalladium (107.4 mg, 9.3×10⁻⁵ moles) as catalyst. The reaction mixture was stirred at room temperature under nitrogen for 4.5 hrs. The reaction mixture was then partitioned between dichloromethane and water while cold and the water layer was separated. The procedure was repeated and the water phases were combined, washed with ethyl acetate, and concentrated in vacuo. The product was purified by reverse phase chromatography using 3×500 micron plates, eluting with 30% tetrahydrofuran in water. After extraction and lyophilization, the product was repurified using the above procedure, but eluting with 10% ethanol in water, to give 58.1 mg of final product (17), a 17.5% yield.

EXAMPLE 11

(5R, 6S)-6-(1-(R)-hydroxyethyl)-2-(4′-N-methyl-N-pyrrolidiniummethylphenyl)carbapenem-3-carboxylate

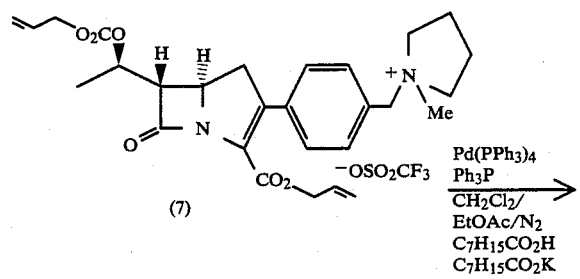

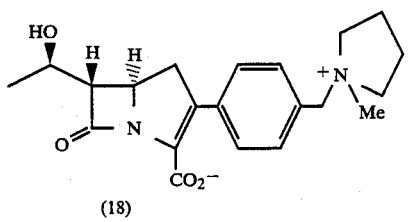

To a stirred solution of compound (7) (326.9 mg, $5.07 \times 10^{-4}$ moles) in 6 ml of sieve dried dichloromethane and 6 ml of ethyl acetate at room temperature there was added sequentially neat 2-ethylhexanoic acid (72.2 mg, $5 \times 10^{-4}$ moles), potassium 2-ethylhexanote (1ml, $5 \times 10^{-4}$ moles) in ethyl acetate, and then a mixture of solid triphenylphosphine (35.4 mg, $1.35 \times 10^{-4}$ moles) and tetrakistriphenylphosphinepalladium (51.9 mg, $4.5 \times 10^{-5}$ moles) as catalyst. The reaction mixture was stirred at room temperature under nitrogen for about 3.5 hrs, after which it was partitioned between dichloromethane and water in the cold. The aqueous phase was separated and washed with water, and the combined aqueous extracts were filtered through a Gelmann filter and then concentrated. The product was purified by reverse phase chromatography using 2×500 micron plates, eluting with 40% tetrahydrofuran in water, under cold conditions, followed by lyophilization to give 74.8 mg of final product (18), a 39.9% yield.

EXAMPLES 12-21

As previously indicated, the penultimate products of Examples 3-9 may be deblocked in accordance with the procedures described in Examples 10 and 11 to give the final products set out in Table I below, which also includes three other compounds of the present invention prepared in accordance with the procedures described above.

TABLE I

| Example No. | ⟨N⟩ group | $\lambda_{max}^{H2O}$ (nm) | Alkylation Method |
|---|---|---|---|
| 12 | -CH₂-N(piperazine)-N-Me | 305 | A |
| 13 | -CH₂-N(thiomorpholine) | 303 | A |
| 14 | -CH₂-N(piperazine)-N⁺(Me)₂ | 302 | — |
| 15 | -CH₂-N(pyrrolidine)-OH | 303 | A |
| 16 | -CH₂-N(morpholine) | 303 | A |
| 17 | -CH₂-N(thiomorpholine S-oxide) | 303 | — |
| 18 | -CH₂-N(piperazine)-N⁺(Me)(O⁻) | 302 | — |
| 19 | -CH₂-N⁺(Me)(morpholine) | 305 | B |
| 20 | -CH₂-N(piperidine) | 304 | A |
| 21 | -CH₂-N⁺(Me)(piperidine) | 305 | B |

What is claimed is:
1. A compound of the formula:

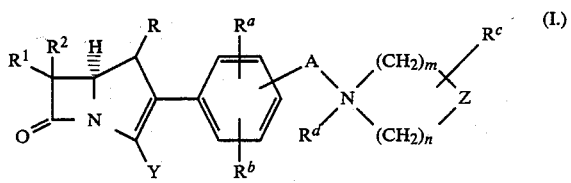 (I.)

wherein:

R is H or CH₃;

R¹ and R² are independently H, CH₃—, CH₃CH₂—, (CH₃)₂CH—, HOCH₂—, CH₃CH(OH)—, (CH₃)₂C(OH)—, FCH₂CH(OH)—, F₂CHCH(OH)—, F₃CCH(OH)—, CH₃CH(F)—, CH₃CF₂—, or (CH₃)₂C(F)—;

$R^a$, $R^b$, and $R^c$ are independently selected from the group consisting of
(a) a trifluoromethyl group: —CF₃;
(b) a halogen atom: —Br, —Cl, —F, or —I;
(c) C₁–C₄ alkoxy radical —OC₁₋₄ alkyl;
(d) a hydroxy group: —OH;
(e) (C₁–C₆ alkyl) carbonyloxy radical:

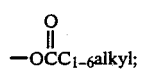

(f) a carbamoyloxy radical which is unsubstituted or substituted on nitrogen with one or two C₁–C₄ alkyl groups:

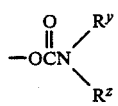

where $R^y$ and $R^z$ are independently H or C₁₋₄ alkyl,
(g) a C₁–C₆ alkylthio radical, C₁–C₆ alkylsulfinyl radical or C₁–C₆ alkylsulfonyl radical:

alkyl where n=0–2, and the alkyl portion is optionally substituted by cyano;
(h) a sulfamoyl group which is unsubstituted or substituted on nitrogen by one or two C₁–C₄ alkyl groups:

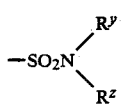

where $R^y$ and $R^z$ are as defined above;
(i) an amino group, or a mono (C₁–C₄ alkyl) amino or di(C₁–C₄ alkyl)amino group:

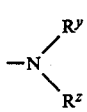

where $R^y$ and $R^z$ are as defined above;

(j) a formylamino group:

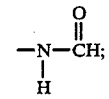

(k) (C₁–C₆ alkyl)carbonylamino radical:

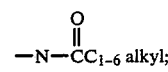

(l) a (C₁–C₄ alkoxy) carbonylamino radical:

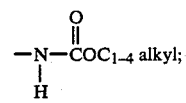

(m) a ureido group in which the terminal nitrogen is unsubstituted or substituted with one or two C₁–C₄ alkyl groups:

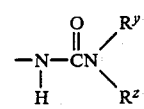

where $R^y$ and $R^z$ are as defined above;
(n) a sulfonamido group:

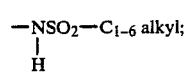

(o) a cyano group; —CN;
(p) a formyl or acetalized formyl radical:

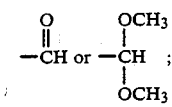

(q) (C₁–C₆ alkyl)carbonyl radical wherein the carbonyl is free or acetalized;

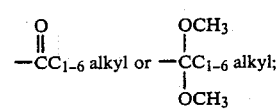

(r) phenylcarbonyl;
(s) a hydroximinomethyl radical in which the oxygen or carbonatom is optionally substituted by a C₁–C₄ alkyl group;

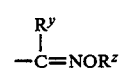

where $R^y$ and $R^z$ are as defined above;
(t) a (C₁–C₆ alkoxy)carbonyl radical;

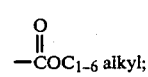

(u) a carbamoyl radical which is unsubstituted or substituted on nitrogen by one or two $C_1$-$C_4$ alkyl groups;

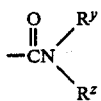

where $R^y$ and $R^z$ are as defined above;
(v) an N-hydroxycarbamoyl or N($C_1$-$C_4$ alkoxy)-carbamoyl radical in which the nitrogen atom may be additionally substituted by a $C_1$-$C_4$ alkyl group;

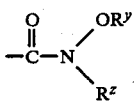

where $R^y$ and $R^z$ are as defined above;
(w) a thiocarbamoyl group:

(x) an amidino group

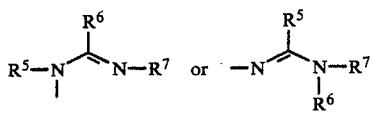

where $R^5$, $R^6$ and $R^7$ are independently hydrogen, $C_1$-$C_4$alkyl or wherein two of the alkyl groups together form a $C_2$-$C_6$alkylidene radical optionally interrupted by a heteroatom and joined together to form a ring;
(y) a carboxamidino group

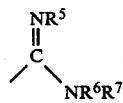

where $R^5$, $R^6$ and $R^7$ are as defined above;
(z) a guanidinyl group where $R^6$ in (a) above is $NR^8R^9$ and $R^8$ and $R^9$ are as defined for $R^5$ through $R^7$ above;
(aa) hydrogen;
(ab) $C_2$-$C_6$ alkenyl radical;
(ac) an unsubstituted or substituted $C_2$-$C_6$ alkynyl radical;
(ad) $C_3$-$C_7$ cycloalkyl radical;
(ae) $C_3$-$C_7$ cycloalkyl methyl radical;
(af) $C_5$-$C_7$ cycloalkenyl radical;
(ag) phenyl, except that only $R^c$ may be phenyl;
(ah) $C_1$-$C_6$ alkyl radical;
(ai) $C_1$-$C_4$ alkyl monosubstituted by one of the substituents (a)-(ag) above;
(aj) an anionic function selected from the group consisting of:
phosphono [P=O(OM$^c$)$_2$]; alkylphosphono {P=O-(OM$^c$) [O($C_1$-$C_4$ alkyl)]}; alkylphosphinyl [P=O-(OM$^c$)—($C_1$-$C_4$alkyl)]; phosphoramido [P=O-(OM$^c$)N(R$^y$)R$^z$ and P=O(OM$^c$)NHR$^x$]; sulfino (SO$_2$M$^c$); sulfo (SO$_3$M$^c$); acylsulfonamides selected from the structures CONM$^c$SO$_2$R$^x$, CONM$^c$SO$_2$N(R$^y$)R$^z$, SO$_2$NM$^c$CON(R$^y$)R$^z$; and SO$_2$NM$^c$CN, where R$^x$ and the phenyl is optionally mono substituted by R$^q$; M$^c$ is hydrogen or an alkali metal; R$^y$ and R$^z$ are as defined above; where
R$^q$ is a member selected from the group consisting of —OH; —OCH$_3$; —CN; —C(O)NH$_2$; —OC(O)NH$_2$; —OC(O)N(CH$_3$)$_3$)$_2$; —SO$_2$NH$_2$; —SO$_2$N(CH$_3$)$_2$; —SOCH$_3$; —F; —CF$_3$; tetrazolyl; and —COOM$^a$, where M$^a$ is hydrogen, alkali metal, methyl or phenyl;
R$^d$ is $C_1$-$C_4$ alkyl, making the nitrogen atom of the N-heterocyclyl moiety to which it is attached quaternary; or it may be absent;
A is para (p) or meta (m) with respect to the point of attachment of the phenyl ring to the carbapenem nucleus, and is (CH$_2$)$_m$—Q—(CH$_2$)$_n$, where m is 0 to 2 and n is 1 or 2; and Q is a covalent bond;
Z is a member selected from the group consisting of CH$_2$, O, S, SO, SO$_2$, N(R') and +N(R')(R''), where R' and R'' are independently hydrogen, $C_1$-$C_4$ alkyl, or oxo; provided that where R$^d$ is not absent, Z cannot be +N(R')(R'');
m is 2 or 3;
n is 1 or 2; and
Y is selected from:
(i) COOH or a pharmaceutically acceptable ester thereof;
(ii) COOM wherein M is an alkali metal or other pharmaceutically acceptable salt;
(iii) COOM wherein M is a negative charge in the case where a permanent positive charge exists elsewhere in the molecule.

2. A compound according to claim 1 wherein R$^1$/R$^2$ is H— and R$^2$/R$^1$ is CH$_3$CH(OH)—.

3. A compound according to claim 1 wherein R$^1$/R$^2$ is H— and R$^2$/R$^1$ is CH$_3$CH(OH)—; and A is —CH$_2$—.

4. A compound according to claim 1 wherein R$^1$/R$^2$ is H— and R$^2$/R$^1$ is CH$_3$CH(OH)—; A is —CH$_2$—; and R$^c$, R$^d$, Z, m and n are selected in such a manner that the following structures result:

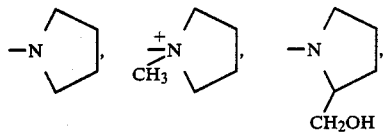

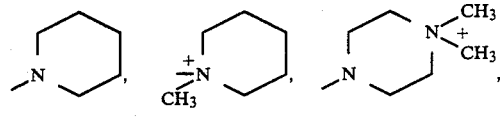

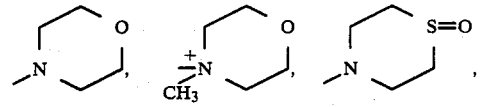

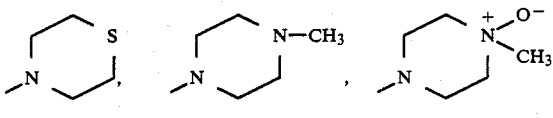

5. A pharmaceutical composition for antibacterial use comprising an antibacterially effective amount of a compound of claim 1 and a pharmaceutically acceptable carrier therefor.

6. A method of treating bacterial infections in human or animal subjects in need of such treatment comprising administering to such subject an antibacterially effective amount of a compound of claim 1.

7. The combination of a compound of claim 1 and a DHP inhibitor.

8. The combination of a compound of claim 4 and the DHP inhibitor 7(L-2-amino 2-carboxyethyl thio)-2(2,2-dimethylcyclopropanecarboxamide)-2-heptenoic acid.

9. A pharmaceutical composition for antibacterial use comprising an antibacterially effective amount of a compound of claim 1, an inhibitorily effective amount of a DHP inhibitor, and, a pharmaceutically acceptable carrier therefor.

10. A pharmaceutical composition according to claim 9 wherein the DHP inhibitor is 7-(L-2-amino-2-carboxyethylthio)-2-(2,2-dimethylcyclopropanecarboxamide)-2-heptenoic acid.

11. A method of treating bacterial infections in human or animal subjects in need of such treatment comprising coadministering to such subject an antibacterially effective amount of a compound of claim 1 and an inhibitorily effective amount of a DHP inhibitor.

12. A method according to claim 11 wherein the DHP inhibitor is 7-(L-2-amino-2-carboxyethylthio)-2-(2,2-dimethylcyclopropanecarboxamide)-2-heptenoic acid.

* * * * *